United States Patent
Anumba et al.

(10) Patent No.: US 12,310,753 B2
(45) Date of Patent: *May 27, 2025

(54) APPARATUS AND METHODS FOR DETERMINING FORCE APPLIED TO THE TIP OF A PROBE

(71) Applicant: THE UNIVERSITY OF SHEFFIELD, Sheffield (GB)

(72) Inventors: Dilichukwu Anumba, Sheffield (GB); Timothy James Healey, Sheffield (GB)

(73) Assignee: THE UNIVERSITY OF SHEFFIELD, Sheffield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/138,387

(22) Filed: Apr. 24, 2023

(65) Prior Publication Data

US 2023/0355178 A1    Nov. 9, 2023

Related U.S. Application Data

(63) Continuation of application No. 16/065,209, filed as application No. PCT/GB2016/054008 on Dec. 21, 2016, now Pat. No. 11,660,049.

(30) Foreign Application Priority Data

Dec. 22, 2015  (GB) ..................... 1522672

(51) Int. Cl.
   *A61B 5/0538*   (2021.01)
   *A61B 5/00*     (2006.01)
   *G01R 35/00*    (2006.01)

(52) U.S. Cl.
   CPC .......... *A61B 5/6843* (2013.01); *A61B 5/0538* (2013.01); *A61B 5/4331* (2013.01);
   (Continued)

(58) Field of Classification Search
   CPC ... A61B 5/6843; A61B 5/0538; A61B 5/4331; A61B 5/435; A61B 2562/0219;
   (Continued)

(56) References Cited

U.S. PATENT DOCUMENTS

| | | |
|---|---|---|
| 4,107,599 A | 8/1978 | Preikschat |
| 5,184,624 A | 2/1993 | Brown et al. |

(Continued)

FOREIGN PATENT DOCUMENTS

| | | |
|---|---|---|
| CA | 2492903 A1 | 11/1999 |
| CN | 201341881 Y | 11/2009 |

(Continued)

OTHER PUBLICATIONS

Tidy JA et al., "Accuracy of detection of high-grade cervical intraepithelial neoplasia using electrical impedance spectroscopy with colposcopy", BJOG. Mar. 2013; 1 20(4):400-10; discussion 410-1. doi: 10.1111/1471-0528.12096. Epub Jan. 4, 2013.

(Continued)

*Primary Examiner* — Andrey Shostak
(74) *Attorney, Agent, or Firm* — Meunier Carlin & Curfman LLC

(57) ABSTRACT

An apparatus for determining a force $F_{tip}$ applied to a tip of an electrical impedance spectroscopy probe includes a load cell, accelerometer, and a processing means. The probe tip has a substantially planar distal end for contacting human or animal tissue. The load cell measures the force $F_{loadcell}$ applied axially along a longitudinal axis when the probe tip is in contact with human or animal tissue. The accelerometer measures a gravity vector $A_{axial}$. The apparatus includes a means for compensating for the mass of the probe tip using the measured force and the gravity vector to produce a calibrated measurement force F applied to the probe tip.

9 Claims, 2 Drawing Sheets

(52) U.S. Cl.
CPC ............ *G01R 35/005* (2013.01); *A61B 5/435* (2013.01); *A61B 2562/0219* (2013.01); *A61B 2562/0252* (2013.01); *A61B 2562/0261* (2013.01)

(58) Field of Classification Search
CPC .... A61B 2562/0252; A61B 2562/0261; A61B 5/035; A61B 5/053; A61B 5/6885; G01R 35/005; G01L 5/0038; G01L 5/0066
See application file for complete search history.

(56) References Cited

U.S. PATENT DOCUMENTS

| | | | |
|---|---|---|---|
| 5,311,878 A | 5/1994 | Brown et al. | |
| 5,919,142 A | 7/1999 | Boone et al. | |
| 6,045,517 A * | 4/2000 | Williams | A61B 5/4528 600/595 |
| 6,258,024 B1 * | 7/2001 | van Der Weegen | A61B 1/32 600/116 |
| 8,262,575 B2 | 9/2012 | Davies | |
| 2002/0106681 A1 | 8/2002 | Wexler et al. | |
| 2003/0164708 A1 * | 9/2003 | Park | G01N 27/07 324/439 |
| 2003/0195400 A1 | 10/2003 | Glukhovsky | |
| 2005/0151545 A1 | 7/2005 | Park et al. | |
| 2006/0100488 A1 | 5/2006 | Davies | |
| 2007/0167819 A1 * | 7/2007 | Osborn, III | A61B 5/224 600/462 |
| 2007/0168127 A1 | 7/2007 | Zaruba et al. | |
| 2008/0262375 A1 | 10/2008 | Brown et al. | |
| 2009/0005707 A1 | 1/2009 | Sarvazyan et al. | |
| 2009/0171234 A1 * | 7/2009 | Gurewitsch | A61B 17/42 600/547 |
| 2009/0306535 A1 | 12/2009 | Davies | |
| 2010/0156656 A1 | 6/2010 | Duarte et al. | |
| 2011/0146405 A1 | 6/2011 | Orleskie | |
| 2011/0263950 A1 | 10/2011 | Larson et al. | |
| 2012/0116242 A1 | 5/2012 | Mahajan et al. | |
| 2012/0157817 A1 | 6/2012 | Tucker | |
| 2012/0157866 A1 | 6/2012 | Ross et al. | |
| 2012/0187000 A1 * | 7/2012 | Kahn | G01N 27/3335 205/782 |
| 2012/0245436 A1 | 9/2012 | Rutkove et al. | |
| 2013/0006136 A1 | 1/2013 | Biancolillo et al. | |
| 2013/0217979 A1 * | 8/2013 | Blackadar | A61B 5/1123 600/301 |
| 2014/0114193 A1 * | 4/2014 | Anthony | A61B 8/429 600/459 |

FOREIGN PATENT DOCUMENTS

| | | |
|---|---|---|
| EP | 1703286 A1 | 9/2006 |
| EP | 1750135 A1 | 2/2007 |
| FR | 2621396 A1 | 4/1989 |
| GB | 2272526 A | 5/1994 |
| GB | 2500176 A | 9/2013 |
| JP | 862162928 A | 7/1987 |
| JP | 2012061057 A | 3/2012 |
| JP | 2012065791 A | 4/2012 |
| JP | 2012090880 A | 5/2012 |
| JP | 2013013734 A | 1/2013 |
| KR | 20080027003 A | 3/2008 |
| KR | 100822789 B1 | 4/2008 |
| RU | 2146806 C1 | 3/2000 |
| UA | 14968 U | 6/2006 |
| WO | WO-0017863 A1 * | 3/2000 ............. B82Y 25/00 |
| WO | 0167098 A1 | 9/2001 |
| WO | 2004086940 A2 | 10/2004 |
| WO | 2004098389 A2 | 11/2004 |
| WO | 2006/129108 | 12/2006 |
| WO | 2006/129116 | 12/2006 |
| WO | 2013037880 A1 | 3/2013 |

OTHER PUBLICATIONS

Wilson AJ et al., "Mk3.5: a modular, multi-frequency successor to the Mk3a EIS/EIT system", Physiol Meas. Feb. 2001; 22(1):49-54.
Jones, DM et al., "Modelling of epithelial tissue impedance measured using three different designs of probe", Physiol Meas. May 2003;24(2):605-23.
Abdul, S. et al., "A clinical study of the use of impedance spectroscopy in the detection of cervical intraepithelial neoplasia (CIN)", Gynecol Oncol. Dec. 2005;99(3 Suppl 1):S64-6.
Brown, Brian H. et al., "Detection of cervical intraepithelial neoplasia using impedance spectroscopy: a prospective study", BJOG. Jun. 2005;112(6):802-6.
Brown, Brian H. et al., "Impedance spectral measurements made through a membrane infection barrier", Med Biol Eng Comput. Dec. 2006;44(12):1085-91. Epub Nov. 9, 2006.
Balasubramani, L. et al., "The detection of cervical intraepithelial neoplasia by electrical impedance spectroscopy: the effects of acetic acid and tissue homogeneity", Gynecol Oncol. Nov. 2009;115(2):267-71. doi: 10.1016/j.ygyno.2009.08.010. Epub Sep. 9, 2009.
Brown, Brian H., "Electrical impedance tomography (EIT): a review", J Med Eng Technol. May 2003-Jun.;27(3):97-108.
Gonzalez-Correa, CA et al., "Electrical bioimpedance readings increase with higher pressure applied to the measuring probe", Physiol Meas. Apr. 2005;26(2):S39-47. Epub Mar. 29, 2005.
Abdul, S. et al., "The use of electrical impedance spectroscopy in the detection of cervical intraepithelial neoplasia", Int J Gynecol Cancer. Sep. 2006-Oct.;16(5):1823-32.
O'Connell, M.P. et al., "Electrical impedance measurements: an objective measure of prelabor cervical change", Journal of Maternal-Fetal and Neonatal Medicine; Dec. 2003; 14, 6; ProQuest, pp. 389-391.
Anumba, Dilly O., et al., Pages from Reproductive Sciences vol. 18, No. 4 (Supplement), Mar. 2011.
Jokhi, R.P. et al. "Reproducibility and repeatability of measuring the electrical impedance of the pregnant human cervix—the effect of probe size and applied pressure", Biomedical Engineering Online, Biomed Central Ltd., vol. 8, No. 1, Jun. 17, 2009, p. 10.
Jokhi, R.P. et al. "The role of cervical Electrical Impedance Spectroscopy in the prediction of the course and outcome of induced labour", BMC Pregnancy and Childbirth, Biomed Central Ltd., vol. 9, No. 1, Sep. 2, 2009, p. 40.
International Search Report and Written Opinion dated Apr. 3, 2017, from International Application No. PCT/GB2016/054008, 18 pages.
Combined Search and Examination Report under Sections 17 and 18(3) dated Jun. 15, 2016, from Application No. GB1522672.3, 5 pages.
Avis, N.J. et al. "In vitro multifrequency electrical impedance measurements and modelling of the cervix in late pregnancy". Physiol Meas 17Suppl 4A:A97 (1996).
Brown, B.H. et al. "Relation between tissue structure and imposed electrical current flow in cervical neoplasia", Lancet 355(9207):892 (2000), pp. 892-895.
Gandhi, S. et al. "Comparison of human uterine cervical electrical impedance measurements derived using two letrapolar probes of different sizes", Biomed Eng Online 5:62 (2006), pp. 1-7.
Gandhi, S. et al. "Electrical impedance spectroscopy of the cervix in non-pregnant and pregnant women", Eur J Obstet Gynecol ReprodBiol 129:145 (2006), pp. 145-149.
Hoe et al. "Measuring Bioimpedance in the Human Uterine Cervix: Towards Early Detection of Preterm Labor", Proceedings of the 26th Annual Conference of the IEEE EMBS San Francisco, CA, USA. Sep. 1-5 2004, pp. 2368-2372.

* cited by examiner

APPARATUS AND METHODS FOR DETERMINING FORCE APPLIED TO THE TIP OF A PROBE

CROSS REFERENCE TO RELATED APPLICATIONS

This application is a continuation of U.S. patent application Ser. No. 16/065,209, filed on Jun. 22, 2018, which is U.S. National Phase of PCT/GB2016/054008, filed Dec. 21, 2016, which claimed priority to United Kingdom Application No. 1522672.3, filed Dec. 22, 2015, the disclosures of which are incorporated by reference as if set forth fully herein.

TECHNICAL FIELD

The present disclosure relates to the field of apparatus and methods for determining the force applied to the tip of a probe, for example an electrical impedance spectroscopy probe. The claimed apparatus and methods can improve the measurement of electrical conductivity of human or animal tissue particularly, but not exclusively, cervical tissue for determining the likelihood of preterm birth.

BACKGROUND

Premature delivery is the cause of perinatal death of two-thirds of babies that have no structural abnormalities. It poses a huge economic burden on scarce health resources as each very premature baby born costs several tens of thousands of pounds in neonatal care. When born before 28 weeks gestation, 1 in 4 babies develop disability. These disabilities can cost hundreds of thousands of pounds annually to treat. The families also suffer huge psychosocial burdens, one parent often having to give up work to care for a disabled child. Whilst survival of premature babies is improving, the rate of premature delivery is increasing, currently running at 7-12% of all births. There is no reliable means of identifying women who deliver prematurely. Current methods for identifying women at high risk of delivering prematurely such as ultrasound of the cervix and fetal fibronectin determination have limited accuracy in women who have no history of preterm birth. A technique for reliably predicting preterm birth by universal screening is therefore highly desirable.

Electrical impedance spectroscopy (EIS) is a known technique that can be used for assessing cervical pre-cancer as set out in, for example, WO2006/129108 (Brown and Tidy) and WO 2006/129116 (Brown and Tidy). Other publications concerning EIS for cervical investigations include:

Avis (1996). In vitro multifrequency electrical impedance measurements and modelling of the cervix in late pregnancy. Physiol Meas 17 Suppl 4A: A97

Brown (2000). Relation between tissue structure and imposed electrical current flow in cervical neoplasia. Lancet 355 (9207): 892

Gandhi (2006). Comparison of human uterine cervical electrical impedance measurements derived using two tetrapolar probes. Biomed Eng Online 5:62

Gandhi (2006). Electrical impedance spectroscopy of the cervix in non-pregnant and pregnant women. Eur J Obstet Gynecol ReprodBiol 129:145

Hoe et al (2004) Measuring Bioimpedance in the Human Uterine Cervix: Towards Early Detection of Preterm Labor. Proceedings of the 26th Annual Conference of the IEEE EMBS San Francisco, CA, USA. Sep. 1-5 2004.

Jokhi (2009). Reproducibility and repeatability of measuring the electrical impedance of the pregnant human cervix. Biomed Eng Online 8:10; and Jokhi (2009). The role of cervical Electrical Impedance Spectroscopy in the prediction of the course and outcome of induced labour. BMC Pregnancy Childbirth 9:40

The applicant has investigated the value of using EIS to measure the "resistance" of the cervix to very small electrical currents (in other words, the electrical conductivity or bioimpedance of the cervical tissue) to detect changes that may precede premature birth. A serial pilot study of women at high risk of preterm birth showed predictive accuracy for premature delivery before 37 and 34 weeks. However significant measurement error was observed using the EIS technique and it is desired to improve accuracy and repeatability of the measurements. One possible reason for measurement error in the EIS technique is that it is difficult to ensure consistent pressure on the cervical tissue by the EIS probe. The Hoe et al paper mentioned above tackles this problem by using a constant force spring to enable more consistent measurements through a range of applied contact forces. The mucus layer on the cervix affects tissue electrical conductivity, adding further error.

It is an aim of the present invention to address disadvantages associated with the known prior art.

BRIEF SUMMARY OF THE DISCLOSURE

Aspects and embodiments of the invention provide apparatus and methods as claimed in the appended claims.

According to an aspect of the invention there is provided apparatus capable of determining the force applied to the tip of a probe, for example an electrical impedance spectroscopy probe, comprising:

an elongate probe comprising a probe tip attached to a handle, the probe tip having a substantially planar distal end for contacting human or animal tissue;

a load cell located in said handle and capable of measuring a force $F_{loadcell}$ applied axially along a longitudinal axis when said probe tip is in contact with said human or animal tissue;

an accelerometer located in the handle for measuring a gravity vector $A_{axial}$;

processing means for compensating for the mass of the probe tip using said measured force and gravity vector to produce a calibrated measurement of force F applied to said probe tip;

display means for indicating to a user the calibrated measurement of force.

In an embodiment, the processing means is further capable of determining an electrical conductivity of human or animal tissue to which the distal end of the probe tip is applied. Preferably, the human or animal tissue is cervical tissue.

In an embodiment, said load cell comprises four strain gauges in a bridge configuration.

In an embodiment, said accelerometer is an analogue tri-axial MEMS accelerometer.

Said processing means may include analogue to digital converters to digitise the outputs of said load cell and said accelerometer.

In an embodiment, said calibrated measurement of force $F=F_{loadcell}-A_{axial}*(M_{tip}+M_{load})$, where $A_{axial}$ is the output of the accelerometer aligned in the axial direction of the probe tip, $M_{tip}$ is the mass of the probe tip and $M_{load}$ is the free mass of the load cell and other parts connected to the load cell such as the connector for the probe tip.

Preferably, said display means is capable of indicating real-time calibrated measurements of force applied to the probe tip.

In an embodiment, said display means includes threshold indications indicating whether too much or too little force is being applied to the probe tip.

The apparatus may further include recording means for recording measurements to facilitate a repeatable application of force to the probe tip.

According to another aspect of the invention there is provided a method of determining the force applied to the tip of a probe, for example an electrical impedance spectroscopy probe, using apparatus as claimed in any of the preceding claims, the method including the steps of:
- obtaining a raw load cell output;
- obtaining a raw accelerometer output;
- obtaining the mass of the probe tip;
- obtaining the area of the distal end of the probe tip;
- applying the distal end of the probe tip to human or animal tissue and measuring a force $F_{loadcell}$ applied axially along a longitudinal axis when said probe tip is in contact with said human or animal tissue;
- using said accelerometer to measure a gravity vector $A_{axial}$;
- using said processing means to compensate for the mass of the probe tip using said measured force and gravity vector to produce a calibrated measurement of force F applied to said probe tip;
- using said display means to indicate to a user the calibrated measurement of force.

Further features are defined in the appended claims.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend an originally filed claim to depend from and/or incorporate any feature of any other claim although not originally claimed in that manner.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

One or more embodiments of the invention will now be described, by way of example only, with reference to the accompanying drawing in which.

DETAILED DESCRIPTION

Figure 1:
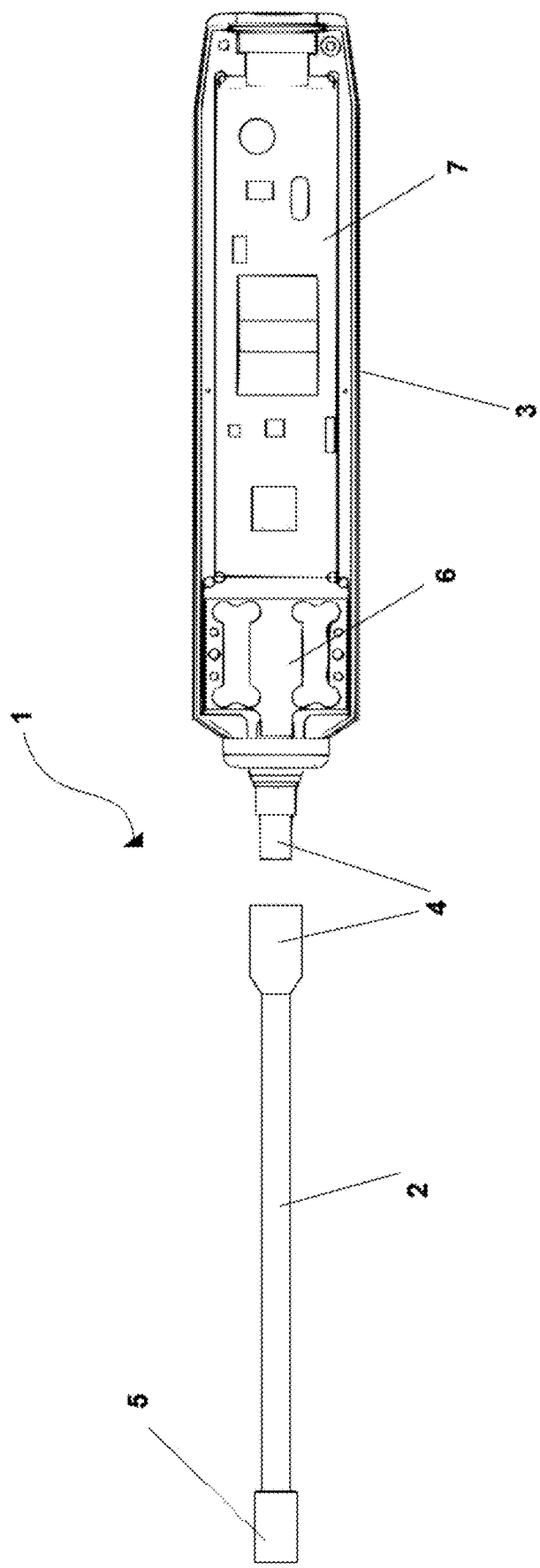
FIG. 1 is a schematic representation of an elongate probe for use in an embodiment of the invention.

FIG. 1 shows an elongate probe 1 which has a handle 3 attached to a probe tip 2. The probe tip can be attached to the handle using a standard commercial connector arrangement 4. The probe tip 2 may be removeably attached to the handle 3 so that the clinician can select and interchange different probe tips for different patients. The probe tip 2 has a substantially planar distal end 5 which includes an arrangement of electrodes, for example a tetrapole arrangement of known type for use in electrical impedance spectroscopy.

A load cell 6 is located in the handle 3. A triaxial MEMS accelerometer 7 is also provided in the handle 3 of the probe 1 and, hence, is in a fixed relationship to both the probe tip 2 and the load cell 6. The handle may also include a processor (microcontroller) 8, a display 9 and a data recorder 10 for recording measurements produced by said load cell and said accelerometer.

The EIS technique involves placing the distal end 5 of the probe tip 2 against the tissue whose electrical conductivity it is desired to measure. The pressure applied by the clinician as the probe tip is placed on the tissue is important as differences in applied pressure significantly affect the results. The changes in cervical tissue measured as an indicator of pre-term birth are more subtle and hence more prone to being affected by the applied pressure than the pre-cancerous changes which are more usually measured by the EIS technique. Consequently it is not only important to be able to repeat the same applied pressure when taking sequential measurements but it is also important to apply pressure within predetermined thresholds.

The apparatus described herein facilitates this by providing the clinician or other user with a display means 9 indicating the applied pressure and indicating whether that applied pressure is within a desired range. This could be done by a bar graph or a traffic light indicator, for example, with a green light displayed when the applied pressure is within a desired range. Alternatively or in addition, an audible alarm or other signal may be provided.

The apparatus described herein is able to compensate for the mass of the probe tip 2 in order to measure (and display) a calibrated measurement of the applied force which is more accurate than a direct measurement of the force applied at the probe tip. The probe tip 2 has a known mass which, due to the action of gravity, could apply a force (dependent on the orientation of the probe) that significantly affects the accuracy of the direct measurement.

It is only necessary to measure the applied force at the probe tip 2 in order to determine the applied pressure because the probe tip has a known area at its distal end 5 (and P=F/A).

The load cell 6 measures the force applied axially along the longitudinal axis of the probe tip. This force is equal to the force applied to the probe tip together with the mass of the tip multiplied by gravity and resolved in the axial direction. The mass of the probe tip is known and the local gravity vector with respect to the probe $A_{axial}$ is measured using the accelerometer. It is therefore possible in this way to obtain a calibrated measurement of the force applied to the probe tip which compensates for the mass of the tip.

In the illustrated embodiment, the load cell 6 comprises four foil strain gauges arranged in a bridge configuration. The bridge can be excited by bursts of square wave pulses at a frequency of 1 kHz which allows the detection of the small resistance change of the load cell bridge with both low power requirements and low sensitivity to DC drift. The output of the bridge can be amplified by and filtered with a Sallen and Key circuit, whose output can be sampled many times per cycle by a microcontroller's 8 analogue to digital converter circuit. Other methods of electrically measuring force would be suitable for this application and understood by the skilled reader.

In the illustrated embodiment, the accelerometer 7 is an Analog Devices® tri-axial MEMS device whose output is suitable for direct connection to the microcontroller's 8 analogue to digital converter circuit. The only signal processing required is simple linear calibration for zero and range. The calibrated tri-axial output of the accelerometer 7 is operated on by a rotation matrix so that it can be accurately aligned with the longitudinal axis of the probe 1. Other methods of measuring the gravity vector resolved to the longitudinal axis of the probe would be suitable for this application and understood by the skilled reader.

The mass of the probe tip can be measured with a balance and stored in an EEPROM within the probe tip 2. Probe tips 2 can be easily interchangeable because the probe 1 can read the mass for each specific probe tip 2 from its EEPROM. The free mass of the load cell 6 can be found by a calibration process wherein the probe 1 is held in two orientations. It is possible to do a full automatic load cell calibration using the known mass of the probe tip 2 and the output of the accelerometer 7, by asking the user to hold the probe 1 in different positions.

A display means 9 (gives the clinician feedback as to whether the force applied to the probe tip 2 is within acceptable limits. The display means could be a five LED bar graph wherein the central LED is highlighted to indicate the desired pressure and progressively more LEDs are lit as the pressure is increased. The range of pressure thresholds required to light each of the LEDS are programmable.

The probe 1 can be set only to take EIS measurements when the pressure is within acceptable limits. An LED bar graph is intuitive to use and, under test, allowed the hand-held probe 1 to maintain EIS measurements within the limits of +−6% of the desired force.

Figure 2:
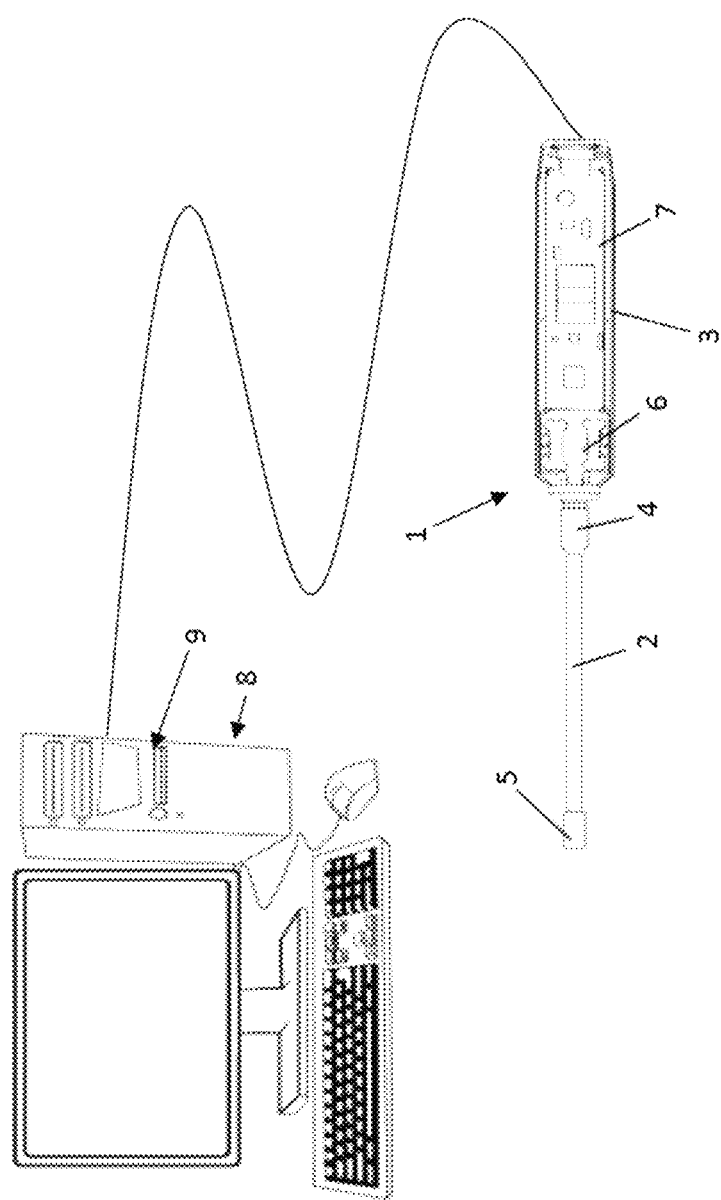
FIG. 2 is a schematic representation of an elongate probe and processing means for use as an embodiment of the invention.

As illustrated in FIG. 2, the processing means are provided, for example, in the form of a PC 8, which can record patient information, e.g., via a recording means 10, guide the clinician through the measuring process, control the probe, analyse and save the results in a database.

Although the description above is in relation to an EIS probe, the apparatus and force measurement technique described herein can be used in other applications. For example, the apparatus could be used to determine the force applied to the tip of a probe used in joint surgery to assess the quality of fit of a new joint. Other applications can be envisaged.

The invention claimed is:

1. An apparatus comprising an elongate probe, said elongate probe being an electrical impedance spectroscopy probe for investigating the electrical conductivity or bioimpedance of cervical tissue, the apparatus capable of determining a force $F_{tip}$ applied to the tip of said elongate probe, the apparatus comprising:
a handle;
said elongate probe comprising said probe tip attached to said handle, wherein the probe tip comprises an EEPROM within the probe tip and wherein a mass of the probe tip is stored on the EEPROM;
a load cell located in said handle and capable of measuring a force $F_{loadcell}$ applied axially to said probe tip along a longitudinal axis thereof when said probe tip is in contact with said human or animal cervical tissue, wherein said load cell comprises four strain gauges in a bridge configuration, wherein the bridge configuration is excited by bursts of square wave pulses at a frequency of 1 kHz;
an accelerometer located in the handle for measuring a gravity vector $A_{axial}$, the accelerometer in fixed relationship with the probe tip and the load cell; and
a microcontroller for compensating for the mass of the probe tip using said measured force and gravity vector to produce a calibrated measurement of said force $F_{tip}$ applied to said probe tip, the microcontroller generating a displayable output for indicating to a user the calibrated measurement of said force $F_{tip}$;
wherein said probe tip is an interchangeable probe tip removably attached to said handle.

2. The apparatus as claimed in claim 1, wherein microcontroller is further capable of determining an electrical conductivity of said human or animal cervical tissue to which the distal end of the probe tip is applied.

3. The apparatus as claimed in claim 1, wherein said accelerometer is an analogue tri-axial MEMS accelerometer.

4. The apparatus as claimed in claim 1, wherein the microcontroller includes analogue to digital converters to digitize outputs of said load cell and said accelerometer.

5. The apparatus as claimed in claim 1, wherein said calibrated measurement of force $F_{tip}=F_{loadcell}-A_{axial}*(M_{tip}+M_{load})$, where $A_{axial}$ is a component of an output of the accelerometer corresponding to the axial-aligned direction of the probe tip, $M_{tip}$ is the mass of the probe tip and $M_{load}$ is the free mass of the load cell and a connector for the probe tip.

6. The apparatus as claimed in claim 1, wherein said displayable output is capable of indicating real-time calibrated measurements of force applied to the probe tip.

7. The apparatus as claimed in claim 1, wherein said displayable output includes threshold indications configured for indicating whether too much or too little force is being applied to the probe tip.

8. The apparatus as claimed in claim 1, further including recording means for recording measurements produced by said load cell and said accelerometer to facilitate a repeatable application of force to the probe tip.

9. The apparatus as claimed in claim 1, wherein the elongate probe takes electrical impedance spectroscopy measurements only when the calibrated measurement of said force $F_{tip}$ is within acceptable limits.

* * * * *